Figure 1:
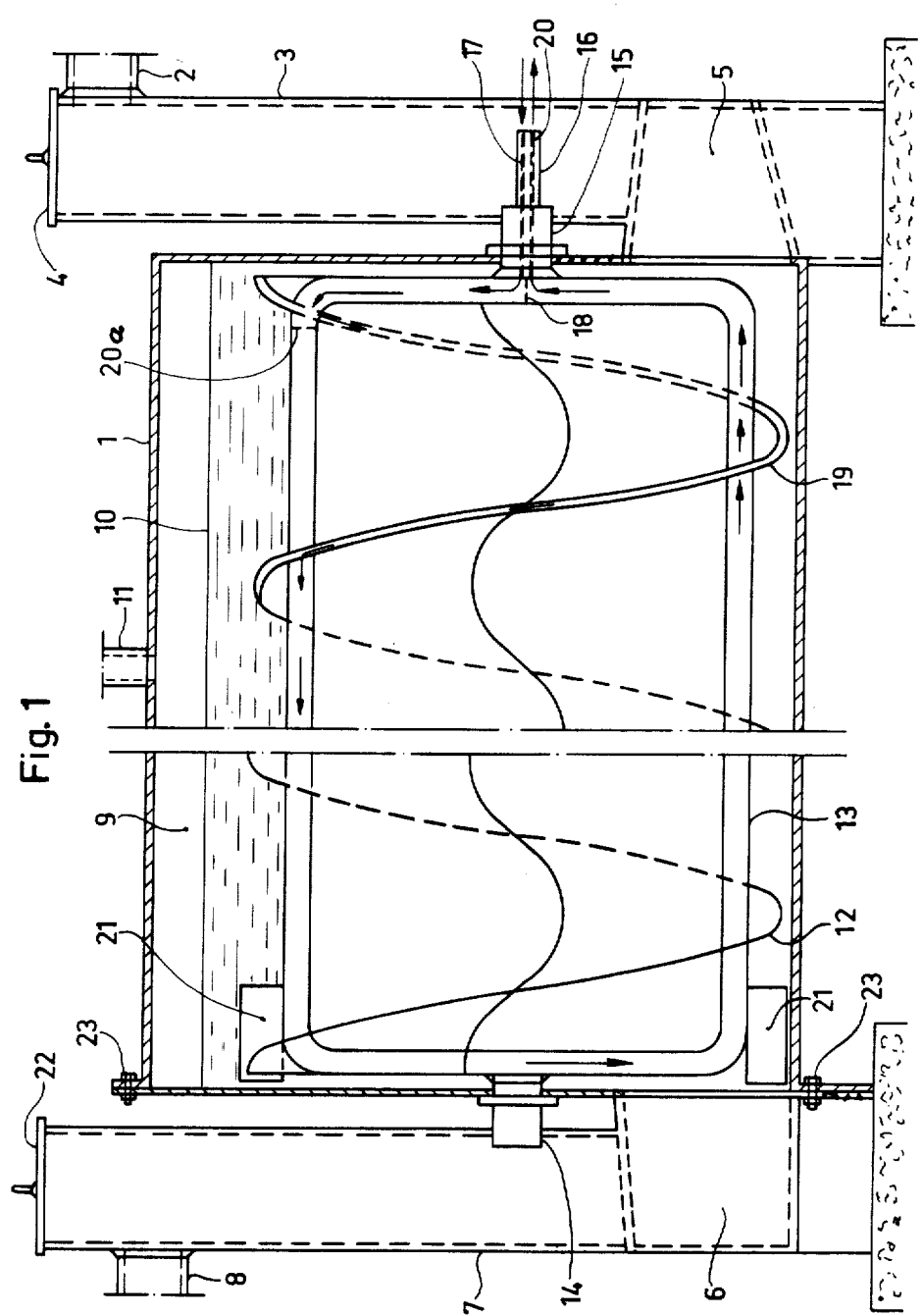

United States Patent [19]

Wikholm et al.

[11] Patent Number: 4,698,310
[45] Date of Patent: Oct. 6, 1987

[54] APPARATUS FOR FERMENTATION OF ORGANIC MATERIAL

[75] Inventors: Bert S. Wikholm, Tullinge; Torsten L. T. Carlsson, Södertälje; Åke R. Öster, Tumba, all of Sweden

[73] Assignee: Alfa-Laval AB, Tumba, Sweden

[21] Appl. No.: 432,920

[22] PCT Filed: Feb. 11, 1982

[86] PCT No.: PCT/SE82/00040

§ 371 Date: Sep. 28, 1982

§ 102(e) Date: Sep. 28, 1982

[87] PCT Pub. No.: WO82/02706

PCT Pub. Date: Aug. 19, 1982

[30] Foreign Application Priority Data

Feb. 11, 1981 [SE] Sweden ................. 8100939

[51] Int. Cl.⁴ ............... C12M 1/02; C12M 1/00; F28F 5/06
[52] U.S. Cl. ................ 435/316; 435/287; 165/87; 165/92
[58] Field of Search ........... 435/287, 316, 305, 801, 435/306, 813, 307; 422/137, 138, 200, 233; 165/87, 92, 93; 48/111

[56] References Cited

U.S. PATENT DOCUMENTS

| 790,467 | 5/1905 | Valerius | 165/92 X |
|---|---|---|---|
| 923,047 | 5/1909 | Hanna | 165/87 |
| 2,610,033 | 9/1952 | Rietz | 165/87 |
| 3,616,747 | 11/1971 | Lapeyre | 165/87 X |
| 3,688,837 | 9/1972 | Ocker | 165/87 |
| 3,701,713 | 10/1972 | Bennett et al. | 435/316 X |
| 4,025,394 | 5/1977 | Young | 435/316 X |
| 4,342,836 | 8/1982 | Harvey | 435/316 |

FOREIGN PATENT DOCUMENTS

| 419494 | 10/1925 | Fed. Rep. of Germany . |
| 0658138 | 3/1938 | Fed. Rep. of Germany . |
| 942034 | 3/1956 | Fed. Rep. of Germany . |
| 3043542 | 7/1982 | Fed. Rep. of Germany ...... 435/316 |
| 0732738 | 9/1932 | France . |
| 1367006 | 6/1964 | France . |
| 2461747 | 2/1981 | France . |
| 2485035 | 12/1981 | France ................ 435/287 |
| 0442458 | 2/1936 | United Kingdom . |

OTHER PUBLICATIONS

Product bulletin, "'Holo-Flite' Processor", the Western Precipitation Corporation, Los Angeles, 10/51.

*Primary Examiner*—Robert J. Warden
*Assistant Examiner*—Randall E. Deck
*Attorney, Agent, or Firm*—Cyrus S. Hapgood

[57] ABSTRACT

A horizontal cylindrical tank contains a conveyor screw rotatable on a horizontal axis below the symmetry axis of the tank, the latter having at its lower part an inlet at one end for organic material and an outlet at the other end for fermented material. A heating medium is circulated through one of the bearings, a frame supporting the screw, and the latter's peripheral portion. The screw moves sludge along the tank bottom toward the outlet and recirculates fermented material back to the inlet region via a space at one side of the screw, while evolved gas discharges through an outlet in the top of the tank.

6 Claims, 2 Drawing Figures

APPARATUS FOR FERMENTATION OF ORGANIC MATERIAL

This invention relates to an apparatus for fermentation of organic material, which is transported substantially horizontally through a fermentor.

An apparatus for this kind is known, for example from the French Patent Specification No. 732738. According to this the material is pushed through the fermentor by gaseous pressure and is heated under its way through the vessel by an internally heated, rotatable pipe coil, which is provided peripherally with blades for stirring the material.

This invention relates to an improvement of the known device with the object to increase the heating efficiency and is characterized by a rotatable screw, provided with blades, which screw carries out the horizontal transport, and by a device for internal heating of the screw blades, at least along a part of the screw elongation.

The advantage with said screw is that its blades given a large heat transfer area and that this area moves in relationship to the material, which is transported and mixed by the screw. These both circumstances give rise to the desired improvement of the heat transfer efficiency.

A further advantage with the invention lies in the following circumstance. For instance when fermenting manure anaerobically gas bubbles containing methane are developed. These lift solid particles to the manure surface, so that there is formed a solid mat. The good mixing, that the screw carries out, prevents the formation of this mat and makes the gas bubbles get free from the particles and collect in the upper part of the fermentor. From there the gas can be discharged.

A further advantage with the transport screw is, that this will efficiently prevent solid material from being accumulated in the fermentor plugging this with the time. The design of the screw makes it prevent the formation of short circuit flows, which could mean lower efficiency in the fermentation process. As the heat requirement of the fermentation process normally prevails in the start end of the fermentor, where the organic material is fed, it can be sufficient to heat the transport screw blades substantially at the inlet of the fermentor. Setting of the desired temperature, for instance 35° C. for anaerobic fermentation, can be done by regulating the temperature and/or the flow of the medium, that is used for heating, such as warm water.

A further improvement of the heating of the content of the fermentor can be obtained by one or a plurality of pipes, oriented in the axial direction of the screw and preferably rotatable with the screw, provided for internal heating. These pipes can be fastened to the screw at the periphery, serving to carry the screw.

It may be desirable to inoculate the material, entering the fermentor, with microorganisms to accelerate the start of the fermenting process. According to one further characterizing feature of the invention this can be achieved by designing the fermentor with a space, located outside the periphery of the screw, which stretches along the screw, which space allows recirculation of fermented material to the material inlet to the fermentor. The recirculation is carried out automatically by returning part of the material, that has reached the gable of the fermentor at the outlet end for the material, moving it outside the screw periphery back towards the inlet side.

The invention shall now be explained more in detail, reference being made to the enclosed drawing, which shows, by way of example, an embodiment of the apparatus in question. To be more exact FIG. 1 shows a longitudinal sectional view of the fermentor and FIG. 2 a cross sectional view of the same apparatus, seen from the left. It is provided that methane gas shall be produced by anaerobic fermentation of manure.

FIG. 1 just shows the both ends of an elongated closed fermentor 1. This is provided with a not shown external heat insulation. Manure is fed through a pipe 2 to an inlet chamber 3, provided with a cap 4, in order that the inner parts of the chamber may be available if needed. From a bottom space 5 in the chamber 3 manure flows further into the fermentor 1, and after having passed this into a bottom space 6 in an outlet chamber 7. Fermented manure then leaves this chamber through a weir outlet 8. In the fermentor there is formed methane gas, which fills a space 9 above the manure surface 10 in the fermentor 1. In the chambers 3 and 7 a manure level will establish, which is higher than the level 10 and which is determined by the gas pressure in the space 9. The developed methane gas is discharged under a certain overpressure through a pipe 11. A transport screw 12 is supported by a rectangular frame 13, consisting of pipes, which frame is welded to the periphery of the screw. The frame is supported at the gables by the fermentor of bearings 14 and 15. The latter bearing is firmly connected to shaft tap 16, which by a motor brings the frame 13 and thus also the screw 12 into rotation. Hot water is fed to the device through a channel 17, which goes through the shaft tap and the bearing 15. In the frame 13 there is provided a blocking wall 18, which in the shown position of the frame directs water upwards through the frame. As is indicated in the figure the left part 19 of the blade of the screw 12 is hollow, and water can—via a connection—reach this hollow blade part from the frame 13. A blocking wall 20a prevents water from flowing further to the left in the upper part of the frame.

According to the figure the cavity of the screw blade ceases after one blade turn and the water flows through a new connection once more into the frame 13 and continues in the frame to the blocking wall 18. Here the water reaches an outlet channel 20 and leaves the apparatus. The frame 13 is provided, at the outlet end, with baffles 21, which help keeping the outlet free and discharge the fermented manure into the space 6. Also the chamber 7 has a cap, denoted 22, which shall again make the inner parts of the chamber available. The chamber 7 and the left gable of the fermentor are also for similar reasons arranged detachable from the rest of the fermentor by a screw joint 23.

Figure 2:
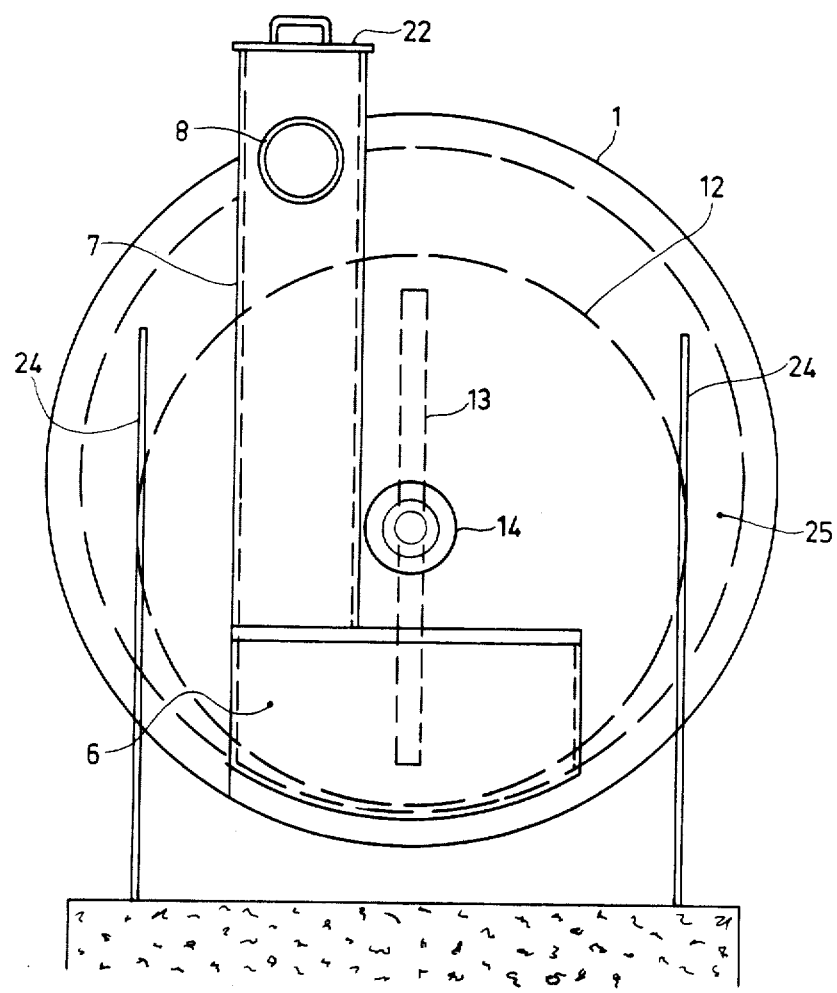

In FIG. 2 corresponding parts have the same reference numbers as in FIG. 1. Furthermore, there are shown in FIG. 2 two rods 24 which support the chamber 7. Furthermore the figure shows a space 25 between the periphery of the screw 12 and the inner side of the fermentor 1. Through this space part of the fermented manure is recirculated from the left gable of the fermentor to the right one, thus inoculating the fresh entering manure with microorganisms.

As well the screw 12 as the frame 13 by rotation break the mat, that would otherwise be formed below the surface 10, especially through the flotating action, that the ascending gas bubbles perform on the solid particles of the manure.

We claim:

1. An apparatus for anaerobic digestion of organic material to produce methane gas and comprising a substantially rigid, horizontal cylindrical tank having a symmetrical axis, a horizontal transport screw, means for heating said screw internally for heat transfer, means mounting said screw for rotation about an axis located below said symmetrical axis of the tank, said tank having an inlet end portion provided with an inlet opening for organic material located below said rotation axis and at the lower portion of the tank, said tank also having an outlet end portion provided with an outlet opening at the lower portion of the tank, said screw having an outer peripheral portion adjacent the tank's bottom and operable to transport sludge along said bottom toward said outlet opening, said peripheral portion of the screw forming with at least one side of the tank an open space for recirculation of fermented material to said inlet end portion, said peripheral portion also forming with the upper part of the tank an accumulation space for evolved gas, said upper part of the tank having an outlet from said accumulation space, said heating means including a pipe frame, wherein the pipe frame mounts the screw and extends parallel to said rotation axis of the screw, and means providing a channel for conveying a heating medium to the pipe frame from outside the tank.

2. The apparatus of claim 1, in which said screw includes heat transfer blades located at said inlet end portion of the tank.

3. The apparatus of claim 1, in which said pipe frame is located at the region of said peripheral portion of the screw.

4. The apparatus of claim 1, comprising also means forming two vertical chambers outside the tank, one of said chambers leading downward to said inlet opening of the tank for supplying organic material thereto, the other of said chambers leading upward from said outlet opening of the tank for discharging fermented material therefrom.

5. An apparatus for anaerobic digestion of organic material to produce methane gas and comprising a substantially rigid, horizontal cylindrical tank having a symmetrical axis, a horizontal transport screw, means for heating said screw internally for heat transfer, means mounting said screw for rotation about an axis located below said symmetrical axis of the tank, said tank having an inlet end portion provided with an inlet opening for organic material located below said rotation axis and at the lower portion of the tank, said tank also having an outlet end portion provided with an outlet opening at the lower portion of the tank, said screw having an outer peripheral portion adjacent the tank's bottom and operable transport sludge along said bottom toward said outlet opening, said pheripheral portion of the screw forming with at least one side of the tank an open space for recirculation of fermented material to said inlet end portion, said peripheral portion also forming with the upper part of the tank an accumulation space for evolved gas, said upper part of the tank having an outlet from said accumulation space, said screw mounting means including bearings at opposite ends of the tank, a hollow frame having a first pair of opposite sides provided with shafts supported in said bearings, respectively, said frame having a second pair of opposite sides located adjacent said peripheral portion of the screw and secured thereto, one of said shafts being hollow and providing for an inlet and a separate outlet for a heating medium, one of said first pair of opposite sides of the frame providing a first passage leading from said medium inlet and providing a second passage leading to said medium outlet, said peripheral portion of the screw forming a helical passage within the screw for conducting the heating medium and spiralling from said inlet end portion of the tank, one end of said helical passage communicating with said first passage and the other end of said helical passage communicating with said second passage.

6. The apparatus of claim 5, in which said second pair of opposite sides and the other of said first pair of sides have hollow portions providing a passage leading from said other end of the helical passage to said second passage.

* * * * *

UNITED STATES PATENT OFFICE
CERTIFICATE OF CORRECTION

PATENT NO. : 4,698,310

DATED : October 6, 1987

INVENTOR(S) : BERT S. WIKHOLM et al.

It is certified that error appears in the above-identified patent and that said Letters Patent are hereby corrected as shown below:

Column 2, lines 30, 31, after "gables" change "by the fermentor of bearings" to --of the fermentor by bearings--.

Signed and Sealed this

Fourteenth Day of June, 1988

Attest:

DONALD J. QUIGG

*Attesting Officer*  *Commissioner of Patents and Trademarks*